(12) United States Patent
Konukseven

(10) Patent No.: US 11,389,250 B2
(45) Date of Patent: Jul. 19, 2022

(54) POSITION DETECTION SYSTEM BY FIBER BRAGG GRATING BASED OPTICAL SENSORS IN SURGICAL FIELDS

(71) Applicant: Erhan Ilhan Konukseven, Ankara (AR)

(72) Inventor: Erhan Ilhan Konukseven, Ankara (AR)

( * ) Notice: Subject to any disclaimer, the term of this patent is extended or adjusted under 35 U.S.C. 154(b) by 210 days.

(21) Appl. No.: 16/634,905

(22) PCT Filed: Dec. 20, 2018

(86) PCT No.: PCT/TR2018/050844
§ 371 (c)(1),
(2) Date: Jan. 29, 2020

(87) PCT Pub. No.: WO2019/209216
PCT Pub. Date: Oct. 31, 2019

(65) Prior Publication Data
US 2020/0229872 A1    Jul. 23, 2020

(30) Foreign Application Priority Data
Dec. 29, 2017 (TR) .................................. 2017/22919

(51) Int. Cl.
*A61B 5/00* (2006.01)
*A61B 34/20* (2016.01)
(Continued)

(52) U.S. Cl.
CPC .............. *A61B 34/20* (2016.02); *A61B 90/50* (2016.02); *G01D 5/35316* (2013.01);
(Continued)

(58) Field of Classification Search
CPC . A61B 34/20; A61B 90/50; A61B 2034/2051; A61B 2034/2055;
(Continued)

(56) References Cited

U.S. PATENT DOCUMENTS

2007/0156019 A1* 7/2007 Larkin ...................... B25J 18/06
    600/104
2008/0218770 A1* 9/2008 Moll ....................... A61B 34/71
    356/614
2017/0202623 A1* 7/2017 Richmond ............ G01B 11/165

FOREIGN PATENT DOCUMENTS

WO    2009023801 A1    2/2009
WO    2012101583 A1    8/2012
(Continued)

*Primary Examiner* — Joel Lamprecht
(74) *Attorney, Agent, or Firm* — Bayramoglu Law Offices LLC

(57) ABSTRACT

A position detection system with fiber Bragg grating based optical sensors in surgical fields that enables real-time detection of the exact coordinates of the location to be operated in the human body in surgical fields. The position detection method with fiber Bragg grating based optical sensors in surgical fields, includes the steps of; obtaining data by Computerized Tomography (CT), Magnetic Resonance Imaging (MRI) and/or any other imaging method, mapping the data with the data received from a fiber Bragg grating based optical sensor device, detecting a position and/or an orientation of any point in an operated region in real-time by mapping the data, transferring the data mapped by defining a plurality of target points during an application and a target point defined by MRI, CT and/or any other imaging method continuously and in real-time to a monitor and/or a plurality of goggles in two and/or three-dimensions.

11 Claims, 1 Drawing Sheet

(51) Int. Cl.
*A61B 90/50* (2016.01)
*G01D 5/353* (2006.01)

(52) U.S. Cl.
CPC ............... *A61B 2034/2051* (2016.02); *A61B 2034/2055* (2016.02); *A61B 2034/2061* (2016.02); *A61B 2034/2065* (2016.02); *A61B 2090/502* (2016.02)

(58) Field of Classification Search
CPC .... A61B 2034/2061; A61B 2034/2065; A61B 2090/502; A61B 2090/372; G01D 5/35316
See application file for complete search history.

(56) References Cited

FOREIGN PATENT DOCUMENTS

| | | | |
|---|---|---|---|
| WO | 2013038301 | A2 | 3/2013 |
| WO | 2013080070 | A1 | 6/2013 |
| WO | 2017158397 | A1 | 9/2017 |

\* cited by examiner

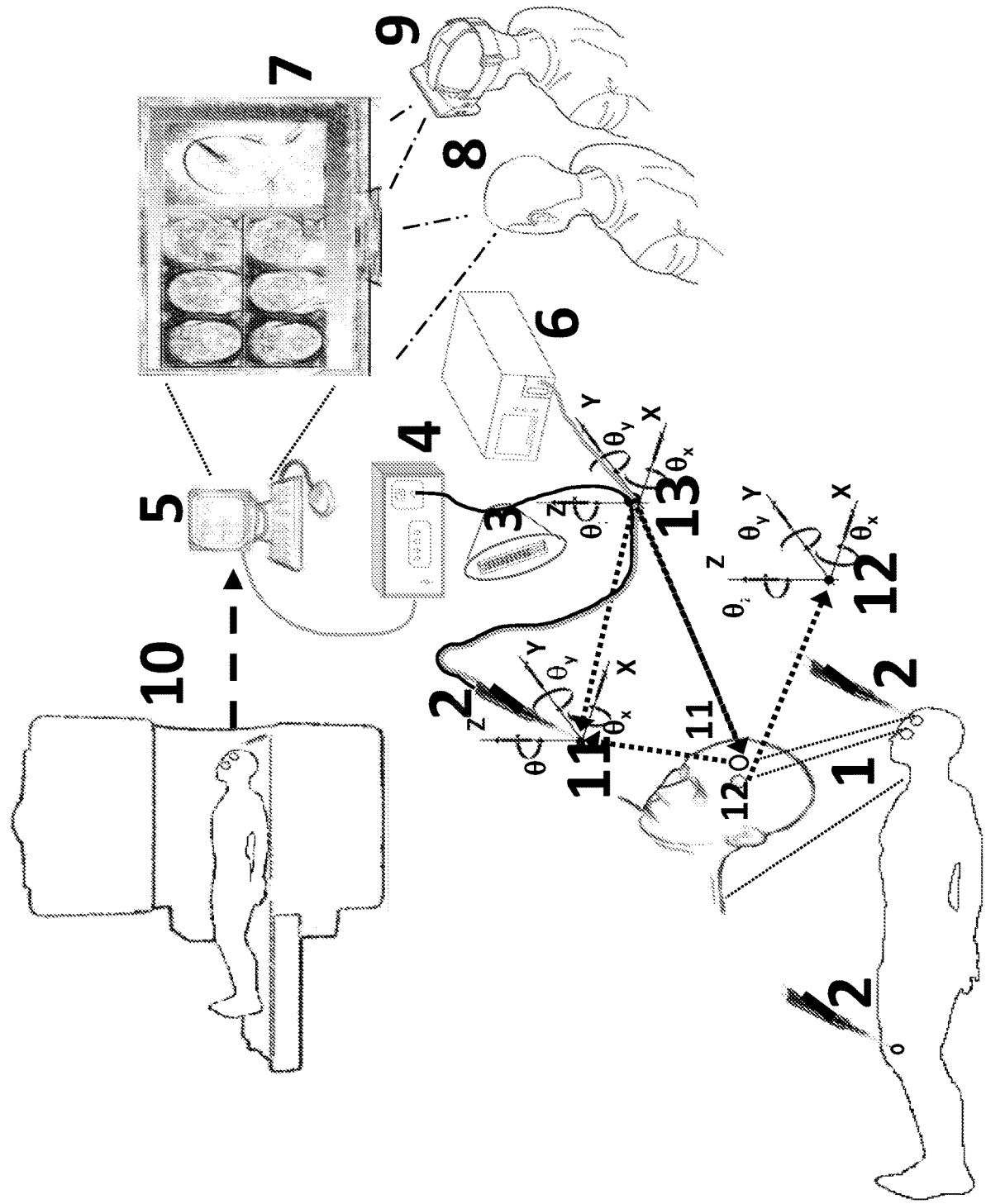

POSITION DETECTION SYSTEM BY FIBER BRAGG GRATING BASED OPTICAL SENSORS IN SURGICAL FIELDS

CROSS REFERENCES TO THE RELATED APPLICATIONS

This application is the national phase entry of International Application No. PCT/TR2018/050844, filed on Dec. 20, 2018, which is based upon and claims priority to Turkish Patent Application No. 2017/22919, filed on Dec. 29, 2017, the entire contents of which are incorporated herein by reference.

TECHNICAL FIELD

The invention subject matter of the application is related to a position detection system that can be used in surgical operations with fiber Bragg grating based optical sensors that enable real-time detection of the exact coordinates of the part of the human body to be intervened.

BACKGROUND

In the medical field, navigation systems and stereotaxic systems are used to find any position and/or direction in the space while advancing from one point to another in any part of the body. These systems are extremely expensive and they can be used only on certain parts of the body. During use of said systems, they do not adapt to changes that may form in the body and they provide the doctor with only pre-surgery or pre-biopsy data information. Moreover, use of such systems are limited and time-wasting due to reasons that they need an extensive calibration procedure, there is a probability that the view angle of the sensor can be blocked and they do not provide continuous/real time feedback position and orientation information mapped on the pre-surgery data.

The patent application with publication Numbered WO2013080070A1 has been found to be related. Said patent application is related to medical imaging and specifically a device and method to insert a surgical port by an endoscopic device. The method, the device and the system was supplied to insert a port by a surgical device related to real-time anatomic data. The endoscopic device comprises fiber optics. The fiber Bragg grating sensors in the fiber optics are used for 3-dimensional shape detection.

The patent application with publication Numbered US 2007156019 A1 has been found to be related. Said patent application is related to the robotic surgery system and the device that comprises position sensors by using fiber Bragg gratings in the fiber optics. The sensor system of the fiber Bragg gratings inside the fiber optics used in the surgical operations in the invention described in the United States patent application provide three-dimensional net position and orientation data for each connection of the surgical device and mapping coordinates for all parts of this device.

SUMMARY

The invention subject to the application is related to the position detection system in surgical fields by fiber Bragg grating based optical sensors that enable real-time detection of exact coordinates of the place to be intervened in the human body.

During surgical operations, the exact coordinates of the point in the human body, the position of the device used in the operation relative to said point and if required the movement angle and/or direction can be detected real-time by the system used in the fiber Bragg grating based optical sensors. The data obtained by Computerized Tomography (CT), Magnetic Resonance Imaging (MRI), DICOM and/or any other imaging method that enable imaging any part of the human body are mapped by an interface software, real-time coordinates of each point is determined and the 2D and/or 3D image of the approaching direction with the determined coordinate are shown real-time on a monitor, projector and/or special goggles to be developed.

The position detection system with fiber Bragg grating based optical sensors in surgical fields enables; real-time detection of the position and orientation of any point in the operation area, identifying target points during biopsy or surgical operation and the desired target points in MRI, CT and/or any imaging method and two and/or three-dimensional transfer of said mapped data to a continuous and real-time monitor and/or goggles by using an interface that maps the data obtained from a CT, MRI and/or any other imaging method and the data received from the fiber Bragg grating based optical sensor through an algorithm on the part of the human body where the biopsy or the surgery will be performed and thus it enables the doctor performing the operation by knowing the position and the direction of the motion (angle) of the used surgical device in the space on the human body continuously/real-time.

By the system that determines the position and orientation of the surgical device used in the surgical field in real-time with said fiber Bragg grating based optical sensors relative to reference points that can be easily specified on the patient during the operation, the error margin is minimized by keeping the tissue integrity in the bone and/or by staying in the tissue in biopsies and tumor surgeries.

A preferred embodiment of the invention comprises the steps;

Obtaining the required data from the part of the human body (1) where the biopsy or the surgical operation will be performed by Computerized Tomography (CT), MRI and/or any other imaging method (10) and transferring said data to a computer (5), Mapping said data with the data obtained from a fiber Bragg grating based optical sensor device (4) by optical fibers with fiber Bragg gratings (3) inside a cable connected to the surgical device (2) to be used in the surgical operation by using an interface through a software run on a computer (5) and defining the Landmarks (Reference Points) (12), Real-time determination of the point where the surgical device (2) contacts the human body (1) and the orientation of the surgical device, Real-time determination of the location (position and/or orientation) (11) of any point on the operated region which is mapped with pre-surgery information, relative to the fiber Bragg reference coordinate system (13), Continuous and real-time transfer of the data in which the MRI, CT and/or any image (10) of the targeted surgical operation region is mapped with the position and orientation where the tip of the surgical device contacts during biopsy or surgical intervention transferred to a monitor (7) and/or goggles in two and/or three-dimensions (8) (9).

Another preferred embodiment of the invention is to know the position and the movement direction (11) of the surgical devices (2) inside the bone and/or tissue in the regions that can't be seen by naked eye or microscope.

Another preferred embodiment of the invention is the real-time 2 and/or 3-dimensional (8) (9) visualization of the important structures that can be encountered while advancing from point A to point B during the biopsy or surgical operation by a monitor (7) and/or goggles.

Another preferred embodiment of the invention has the configuration such that the fiber Bragg reference position (13) can be fixed with the tissue and/or the body forms so that the reference position can be moved together with the tissue and/or the body form where the surgical operation is performed during the biopsy and the surgical operation and the position and/or the orientation (11) (12) of the tip of the surgical device is not affected by the positional changes of the region where the operation is performed.

Another preferred embodiment of the invention enables use of haptic devices in the proposed system to incorporate tactile sense while advancing inside the tissue and/or the bone using the information mapped with pre-surgery data.

BRIEF DESCRIPTION OF THE DRAWINGS

The FIGURE prepared to provide a better understanding of the position detection system with fiber Bragg grating based optical sensors in the surgical fields developed by this invention is described below.

FIG. 1—The position detection system with fiber Bragg grating based optical sensors in the surgical fields.

The parts/elements/components present in the FIGURES prepared to provide a better understanding of the position detection system with fiber Bragg grating based optical sensors in the surgical fields developed by this invention are given individual reference numbers and the description of each number is given below.
1. Patient
2. The device used in the operation
3. Optical Fiber Manufactured by Fiber Bragg Grating Method
4. Fiber Bragg Grating Device
5. Portable Computer
6. Surgical Device (Example: Ultrasonic Surgical Aspirator Device)
7. Monitor
8. Tracking of Position in 2D Monitor without a 3D goggles (Doctor)
9. Tracking of Position with 3D Goggles (3-Dimensional Imaging Device) (Doctor)
10. Imaging Device
11. Coordinate System that shows the Position of the Tip of the Surgical Device (X, Y, Z) and the Orientation of the Device ($\square$x, $\square$y, $\square$z).
12. Landmark (Reference Points) Coordinate System
13. Reference Coordinate System

DETAILED DESCRIPTION OF THE EMBODIMENTS

The invention subject matter of the application is related to a position detection system with fiber Bragg grating based optical sensors (3) that enables real-time detection of exact coordinates (11) of the location to be operated in the human body (1) in surgical fields. Said position detection system with fiber Bragg grating based optical sensors (3) in surgical fields comprises; the patient (1) to be surgically operated, the surgical device (2) of which the position and the orientation is desired to be detected in the surgical operation, the optical fiber (3) of which the reflectivity changes depending on the displacement, the fiber Bragg grating device (4) that determines the position and the orientation (11) of the tip of the device (2) which the fibers (3) are connected to and which is used in the surgical operation relative to the reference (13) in which the fiber Bragg cable is fixed in the space detecting the wavelengths reflected from the fibers (3), the portable computer (5) that contains the user interface and that maps the data obtained by CT, MRI and/or other imaging methods (10) and the data received from the fiber Bragg grating device (4) with respect to Landmarks (reference points) (12), the 3D goggles (9) (the display device that shows the 3-Dimensional and the real environment simultaneously) that shows the data obtained by mapping the data received from CT, MRI and/or other imaging methods and the data received from the Fiber Bragg grating device (4) in 2 or 3-dimensions, the monitor (7) that shows the data obtained by mapping the data received from CT, MRI and/or other imaging methods (11) and the data received from the Fiber Bragg grating device (4) in 2 or 3-dimensions (8).

By the position detection system with the fiber Bragg grating based optical sensors in the surgical fields, the required data is obtained through Computerized Tomography (CT), MRI and/or any other imaging method (10) that is performed on the region where the biopsy or the surgery will be performed on the human body (1). These data is mapped with the data received from the fiber Bragg grating based optical sensor device (4) with the fiber Bragg grating optical fibers (3) in the cable connected to the device (2) to be used in the surgical operation by a software run on a computer (5) by using Landmarks (reference points) (12). The position and orientation (11) of any points in the operated region can be detected in real-time by mapping said data. The desired target points and the target points in the biopsy or the surgical operation that are defined in MRI, CT and/or any other imaging method and the mapped data are transferred continuously and in real-time to a monitor (7) and/or goggles (9) in two and/or three-dimensions. Thus, the doctor (8) performing the operation can perform the operation successfully by knowing the position and the orientation of the movement of the surgical device in the human body continuously/in real-time. The system is not affected by the changes in the position of the tissue and/or the body during biopsy and the surgical operation.

The doctor (8) can know the real-time position (11) of the surgical device (2) used in the operation including the coordinates and the moving direction where he can't see during surgery with naked eye or the microscope inside the bone and/or the tissue. The coordinate, movement angle and the position of the defined surgical devices (2) are transferred continuously and in real-time to a monitor (7) and/or to goggles (9) in two and/or three-dimensions. It is possible to use a haptic device that virtualizes the tactile sense to incorporate the tactile sense while advancing inside the tissue and/or the bone.

3 or more Landmarks (12) (the marker that shows the position of something) to be taken are marked by detecting in CT and/or MRI images (10). If these Landmarks are marked during biopsy or surgical operation, all points can be reached in real-time without any problems with the continuous flow of data. Transfer of this obtained continuous data flow to a monitor (7) and/or goggles (9) in two and/or three-dimensions provide convenience to the doctor (8) who performs the operation visually in real-time.

The proposed system is a first in the medical field and provides a real-time navigation during the operations by constantly providing feedback to the doctor. Moreover, the doctor (8) can see where and in which position and coordinates he/she is inside the tissue in three-dimensions on a monitor (7) and/or goggles (9) where he/she can't see with naked eye and/or under microscope.

By the position detection system with fiber Bragg grating based optical sensors in the surgical fields, the time of the operation is shortened, the success rate of the operation is increased, the operations are performed as planned and the number of C-armed endoscopies in which the patient and the staff is constantly subjected to during the surgery is decreased.

What is claimed is:

1. A method of detecting the position of a surgical device during a surgery using a fiber Bragg grating based optical sensor device comprising:

determining a reference for a fiber Bragg grating based optical sensor device relative to a body by defining a plurality of landmarks on the body when the fiber Bragg grating based optical sensor device is in a specific position relative to the body, wherein the fiber Bragg grating sensor device comprises a plurality of fiber Bragg grating optical fibers positioned inside a cable, wherein the plurality of fibers is positioned along the length of the cable, wherein the plurality of fibers is physically connected to a surgical device during a surgery on an operating area of the body, and wherein the specific position of the fiber Bragg grating based optical sensor device is based on a specific position of the plurality of fibers;

defining a location of the operating area based on imaging data received by an imaging device:

detecting a position of the surgical device based on sensor data received by the fiber Bragg grating based optical sensor device relative to the location of the operating area;

mapping the imaging data received by the imaging device on the location of the operating area with the sensor data received by the fiber Bragg grating based optical sensor device on the position of the surgical device relative to the location of the operating area to detect the position of the surgical device in real-time; and transferring the mapped imaging data and sensor data continuously and in real-time to a display to show the position of the surgical device continuously and in real-time to a member of a surgical team.

2. The method of claim 1, wherein the data received from the fiber Bragg grating based optical sensor device comprises a coordinate or a movement angle of the surgical device.

3. The method of claim 1, wherein defining a location of the operating area based on imaging data obtained by an imaging method comprises determining a plurality of target points of the operating region.

4. The method of claim 1, wherein detecting the position of the surgical device comprises detecting the movement of the surgical device from point A to point B.

5. The method of claim 1, wherein the data received from the sensor is three-dimensional.

6. The method of claim 1, wherein the plurality of landmarks comprises at least three landmarks.

7. The method of claim 1, wherein the plurality of fibers is positioned outside the body.

8. The method of claim 1, wherein the reference does not need to be re-defined when the specific portion of the fiber Bragg grating based optical sensor device is not in the specific position due to movement of tissue or body during the surgery.

9. The method of claim 1, wherein the display comprises a monitor.

10. The method of claim 1, wherein the imaging device comprises computerizing tomography.

11. The method of claim 1, wherein the imaging device comprises magnetic resonance imaging.

* * * * *